United States Patent
de Sousa Martins

(10) Patent No.: US 10,201,508 B2
(45) Date of Patent: Feb. 12, 2019

(54) POSITIVELY CHARGED LIPOSOMES AS LIPOPHILIC MOLECULE CARRIERS

(71) Applicant: Kemin Industries, Inc., Des Moines, IA (US)

(72) Inventor: Diogo de Sousa Martins, Sao Paulo (BR)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 15/431,972

(22) Filed: Feb. 14, 2017

(65) Prior Publication Data

US 2017/0231920 A1   Aug. 17, 2017

Related U.S. Application Data

(60) Provisional application No. 62/295,253, filed on Feb. 15, 2016.

(51) Int. Cl.
| | |
|---|---|
| *A61K 31/45* | (2006.01) |
| *A61K 31/045* | (2006.01) |
| *A61K 9/00* | (2006.01) |
| *A61K 9/127* | (2006.01) |

(52) U.S. Cl.
CPC .......... *A61K 31/045* (2013.01); *A61K 9/0009* (2013.01); *A61K 9/0048* (2013.01); *A61K 9/1272* (2013.01)

(58) Field of Classification Search
CPC ..................................................... A61K 31/45
See application file for complete search history.

(56) References Cited

U.S. PATENT DOCUMENTS

| | | | |
|---|---|---|---|
| 4,186,183 A * | 1/1980 | Steck ..................... | A61K 9/127 264/4.1 |
| 7,109,361 B2 | 9/2006 | Hoffman et al. | |
| 2006/0216251 A1* | 9/2006 | Morariu .................. | A61K 8/41 424/59 |
| 2007/0196284 A1 | 8/2007 | Tournier et al. | |
| 2010/0093648 A1 | 4/2010 | Cruz | |
| 2011/0052678 A1* | 3/2011 | Shantha .............. | A61K 9/0048 424/450 |
| 2011/0064794 A1* | 3/2011 | Deng .................. | A61K 9/1075 424/450 |

OTHER PUBLICATIONS

Hoogevest et al (Eur. J. Lipid Sci. Technol. 2014, 116, 1088-1107).*

(Continued)

*Primary Examiner* — Benjamin J Packard
(74) *Attorney, Agent, or Firm* — Nyemaster Goode

(57) ABSTRACT

A method of producing positively charged liposome vesicles for use as carriers of lipophilic molecules. A mixture of hydrogenated phospholipids, a cationic excipient and a lipophilic molecule are dissolved in a solvent to form a composition. The composition is dried to remove the solvent. The dried composition is hydrated to form liposome vesicles and optionally the liposome vesicles are homogenized to form smaller vesicles. The vesicles are useful for delivery lipophilic molecules, such as, but limited to, lutein and zeaxanthin, to ocular tissues using iontophoresis.

6 Claims, 7 Drawing Sheets

(56) References Cited

OTHER PUBLICATIONS

International Searching Authority, "Search Report and Written Opinion," issued in connection with International Patent Application No. PCT/US17/17763, dated Apr. 27, 2017, 7 pages.
Aman et al., "Application of HPLC coupled with DAD, APcl-MS and NMR to the analysis of lutein and zeaxanthin stereoisomers in thermally processed vegetables," Journal of Food Chemistry, vol. 92, 2005, pp. 753-763.
Fratianni et al., "Degradation of carotenoids in orange juice during microwave heating," Journal of Food Science and Technology, vol. 93, 2010, pp. 867-871.
Frede et al., "Stability and cellular uptake of lutein-loaded emulsions," Journal of Functional Foods, vol. 8C, 2014, pp. 118-127.
Garcia-Parra et al., "Application of innovative technologies, moderate-intensity pulsed electric fields and high-pressure thermal treatment, to preserve and/or improve the bioactive compounds content of pumpkin," Journal of Innovative Food Science and Emerging Technologies, vol. 45, 2018, pp. 53-61.
Lin et al., "Stability of carotenoids in tomato juice during processing," Journal of European Food Research and Technology, vol. 221, 2005, pp. 274-280.
Ma et al., "Influence of technical processing units on the a-carotene, b-carotene and lutein contents of carrot (*Daucus carrot* L.) juice," Journal of Functional Foods, vol. 16, 2015, pp. 104-113.
McInerney et al., "Effects of high pressure processing on antioxidant activity, and total carotenoid content and availability, in vegetables," Journal of Innovative Food Science and Emerging Technologies, vol. 8, 2007, pp. 543-548.
Plaza et al., "Carotenoid and flavanone content during refrigerated storage of orange juice processed by high-pressure, pulsed electric fields and low pasteurization," Journal of Food Science and Technology, vol. 44, 2011, pp. 834-839.
Provesi et al., "Changes in carotenoids during processing and storage of pumpkin puree," Journal of Food Chemistry, vol. 128, 2011, pp. 195-202.
Subagio et al., "Stability of Lutein and Its Myristate Esters," Bioscience, Biotechnology & Biochemistry, vol. 63, Issue 10, 1999, pp. 1784-1786.
International Searching Authority, "Search Report and Written Opinion," issued in connection with International Patent Application No. PCT/US2017/017763, dated Apr. 27, 2017, 6 pages.
International Searching Authority, "International Preliminary Report on Patentability" issued in connection with International Patent Application No. PCT/US2017/017763, dated Aug. 21, 2018, 5 pages.

* cited by examiner

POSITIVELY CHARGED LIPOSOMES AS LIPOPHILIC MOLECULE CARRIERS

RELATED APPLICATIONS

This application claims priority to U.S. Patent Application Ser. No. 62/295,253 filed Feb. 15, 2016, and incorporates the same herein in its entirety by this reference.

BACKGROUND OF THE INVENTION

The present invention relates generally to bioactive liposomes suitable for delivery to tissues and to a method for their production and, more specifically, to positively charged liposomes useful as carriers of lipophilic molecules and particularly for application to deliver lipophilic molecules, such as carotenoids, via iontophoresis to ocular tissues using iontophoresis.

Lutein is associated with reducing the risk of developing AMD (age-related macular degeneration) and cataracts extraction due to its antioxidant and photoprotective effects, and its exclusive distribution in the eye macula [Kijlstra A., Tian Y., Kelly E. R., Berendschot T. T. 2012. Lutein: more than just a filter for blue light. Prog Retin Eye Res. 31:303-315]. Lutein has been widely used through oral supplementation with the rationale that systemic circulation can bring lutein to the coroidal circulation for uptake into the macula, through xanthophyll-binding protein [Yemelyanov A. Y., Katz N. B., Bernstein P. S. 2001. Ligand-binding characterization of xanthophyll carotenoids to solubilized membrane proteins derived from human retina. Exp Eye Res. 72:381-392]. However, several reports demonstrate that only a small percentage of lutein reaches the macula [Bone R. A., Landrum J. T., Guerra L. H., Ruiz C. A. 2003. Lutein and zeaxanthin dietary supplements raise macular pigment density and serum concentrations of these carotenoids in humans. J Nutr. 133:992-998; Landrum J. T., Bone R. A., Joa H., Kilburn M. D., Moore L. L., Sprague K. E. 1997. A one year study of the macular pigment: the effect of 140 days of a lutein supplement. Exp Eye Res. 65:57-62; Ma L., Lin X. M. 2010. Effects of lutein and zeaxanthin on aspects of eye health. J Sci Food Agric. 90:2-12]. Moreover, due to eye barrier limits, therapeutic treatments in the posterior eye segment are difficult. Since the eye is protected by the tear film, corneal, vitreous, blood-retinal and blood-aqueous barriers it is very difficult to deliver drugs to the eye, particularly to the retina, in sufficient concentrations and with minimal side-effects [Barar J., Javadzadeh A. R., Omidi Y. 2008. Ocular novel drug delivery: impacts of membranes and barriers. Expert Opin Drug Deliv. 5:567-581; de la Fuente M., Ravina M., Paolicelli P., Sanchez A., Seijo B., Alonso M. J. 2010. Chitosan-based nanostructures: a delivery platform for ocular therapeutics. Adv Drug Deliv Rev. 62:100-117]. In-situ applications have been used to overcome this problem; however, slow delivery systems such as implants are very invasive and expensive. Recently, intra-vitreous injections of lutein/zeaxanthin have been used to stain specific preretinal membranes and other eye structures [Sousa-Martins D., Maia M., Moraes M., Lima-Filho A. A., Rodrigues E. B., Chen J., Farah M. E., Santos L. B., Belfort R., Jr. 2012. Use of lutein and zeaxanthin alone or combined with Brilliant Blue to identify intraocular structures intra-operatively. Retina. 32:1328-1336; Rodrigues E. B., Costa E. F., Penha F. M., Melo G. B., Bottos J., Dib E., Furlani B., Lima V. C., Maia M., Meyer C. H., Hofling-Lima A. L., Farah M. E. 2009. The use of vital dyes in ocular surgery. Surv Ophthalmol. 54:576-617; Maia M., Furlani B. A., Souza-Lima A. A., Martins D. S., Navarro R. M., Belfort R., Jr. 2014. Lutein: a new dye for chromovitrectomy. Retina. 34:262-272; Badaro E., Furlani B., Prazeres J., Maia M., Lima A. A., Souza-Martins D., Muccioli C., Lucatto L. F., Belfort R., Jr. 2014. Soluble lutein in combination with brilliant blue as a new dye for chromovitrectomy. Graefes Arch Clin Exp Ophthalmol. 252:1071-1078]. This has been the first data on in-situ delivery of lutein towards the macula, exploiting lutein's intrinsic staining effect. Lutein/zeaxanthin potential in delaying AMD progression and potential neuroprotective action shown in different trials has not yet been proven through in-situ application following intraocular delivery. Intra-vitreous injection of lutein with a prevention purpose may be a too invasive way of delivering lutein towards the macula, with the disadvantage of poor patient acceptance.

Iontophoresis is a technology that uses controlled low-level electrical energy to transport ionized drugs through a biological membrane [Eljarrat-Binstock E., Domb A. J. 2006. Iontophoresis: a non-invasive ocular drug delivery. J Control Release. 110:479-489]. Different iontophoresis delivery systems for ophthalmic use have been created and have been used to safely and effectively deliver medication to both the anterior and posterior segments of the human eye [Eljarrat-Binstock E., Domb A. J. 2006. Iontophoresis: a non-invasive ocular drug delivery. J Control Release. 110: 479-489]. With this technology it is possible to delivery significant amounts of macromolecules across the cornea and sclera. What is needed is a novel, stable form of lutein/zeaxanthin that is charged, so the iontophoresis device can propel high concentrations of the charged lutein/zeaxanthin particles transclerally or/and transcorneally. Other lipophilic substances, such as carotenoids, anti-inflammatory molecules or anti-angiogenic compounds, may also be delivered to the eye by iontophoresis using the same vehicle described herein.

SUMMARY OF THE INVENTION

Due to the fact that lutein/zeaxanthin are molecules with a large molecular weight, lipophilic and insoluble in water, the delivery of these carotenoids through iontophoresis without modifications is nearly impossible. In order to overcome that, we developed a formulation with positively charged liposome vesicles that behave as carriers of lutein/zeaxanthin molecules, with the aim of facilitating lutein delivering to the eye. This new product will be used as active ingredient in ocular iontophoretic application. The liposomal structure was formed using hydrogenated phosphatidylcholine in combination with a cationic excipient (octadecylamine) and crystalline lutein/zeaxanthin, while generating a particle that is positively charged, thereby creating a structure capable of transport lutein/zeaxanthin, or other lipophilic molecules, to pass through cornea and sclera cells.

The goal of this work was to develop a new formulation of charged lipossomic lutein (hereupon referred as Lipo+) having a high concentration of lutein. In particular, we analyzed the stability and toxicological profile of this new formulation.

DETAILED DESCRIPTION OF PREFERRED EMBODIMENTS

The term "lipophilic molecule" as used herein refers to compounds which dissolve in lipids, fats, oils and non-polar solvents. The lipophilic molecule may be a pharmaceutically active agent, drug, imaging agent, therapeutic agent, diagnostic agent, compound, or composition. A non-limiting example of a lipophilic molecule is lutein. The lipophilic molecule may comprise between about 0.001% to 10% by weight of the liposome composition. Stated another way, the lipophilic molecule may comprise between about b.cde % to ab % by weight of the liposome composition, wherein a is either 0 or 1 and b, c, d and e are selected from 0, 1, 2, 3, 4, 5, 6, 7, 8 and 9 with the exceptions that all of b, c, d and e are 0 when a is 1 and not all of a, b, c, d and e are 0.

The term "liposomes" as used herein refers to single or multiple concentric lipid bilayers encapsulating an aqueous compartment. The liposome may include natural and/or synthetic lipids and surfactants. The liposomes trap the lipophilic molecule in the lipid membrane. The size of these nearly spherical lipid vesicles of the present invention can range between 50 and 450 nm. Stated another way, the size of the liposomes of the present invention range between about ab nm to about cde nm, wherein a is selected from 5, 6, 7, 8 and 9, b is selected from 0, 1, 2, 3, 4, 5, 6, 7, 8 and 9, c is selected from 0, 1, 2, 3 and 4, d is selected from 0, 1, 2, 3, 4 and 5 and e is selected from 0, 1, 2, 3, 4, 5, 6, 7, 8 and 9 except when c is 4 and d is 5 in which case it is 0. Of course not all of a, b, c, d and e can be 0.

The term "lipid film-forming liquid" as used herein refers to any lipid-containing liquids that form a film upon drying. Non-limiting examples of lipid film-forming liquids include solubilized phospholipids, including lecithin and lysolecithin.

The term "solvent" as used herein refers to solvents in which the lipophilic molecule is soluble and which can be removed by evaporation. Non-limiting examples of solvents are chloroform, methanol and tetrahydrofuran.

The term "cationic excipients" as used herein refers to cationic lipids with hydrocarbon chains having lengths of between about 8 and 18 carbons either saturated or mono-saturated and either mono-valent or multivalent. A non-limiting example of a cationic excipients is octadecylamine.

EXAMPLE

Materials and Methods

Chemicals and reagents. The lipid film was prepared using phospholipon 90H (Lipoid GmbH), octadecylamine (Sigma-Aldrich) and crystalline lutein (Kemin Health, FloraGLO® crystalline lutein) dissolved in chloroform ($CHCl_3$) (Sigma-Aldrich) and methanol (MeOH) (Sigma-Aldrich). Hydration of the lipids was performed by adding i) distilled water (Water Ultrapure—MilliQ—by Aqua-Max—conductivity 0.054 uS/cm); ii) a phosphate buffer solution composed of sodium phosphate monobasic dihydrate (Sigma-Aldrich) and sodium phosphate dibasic dihydrate (Sigma-Aldrich) or iii) these solutions supplemented with Tween 80 (Sigma-Aldrich).

Figure 1:
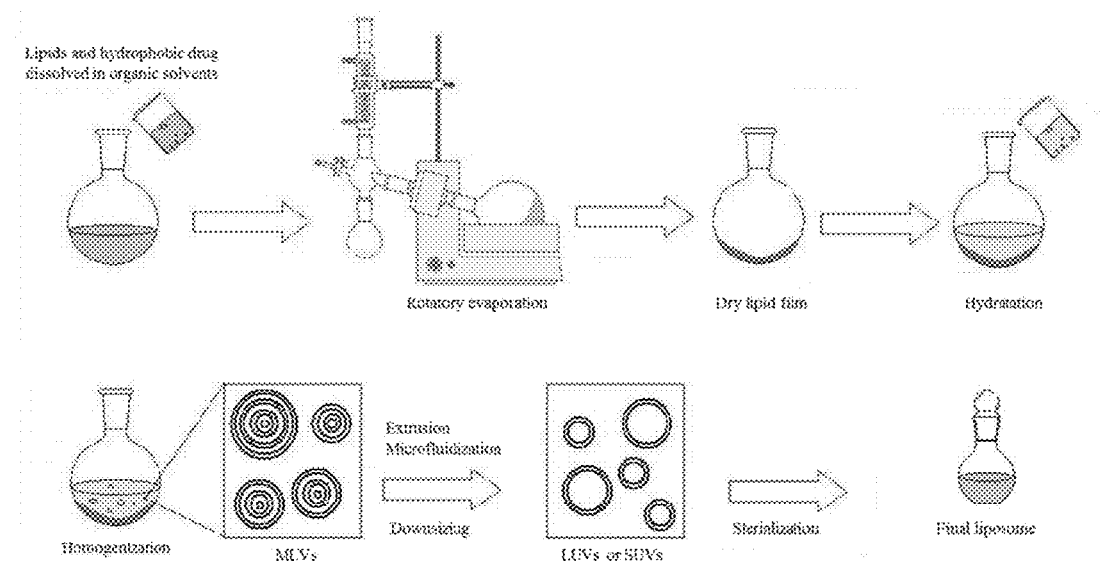
FIG. 1 is a schematic diagram of the liposome production through lipid hydration followed by homogenization and vesicle downsizing; MLVs—multilamellar vesicles, LUVs—large unilamellar vesicles, SUVs—small unilamellar vesicles (adapted from Lopes et al.[13]).

Lutein liposome formulation. In this work, five different formulations of lutein encapsulated in liposomes were prepared (listed in Tables 1, 2 and 3). The lipid film was prepared using phospholipon 90H, octadecylamine and lutein dissolved in $CHCl_3$/MeOH (2:1 v/v). Solvents were removed under vacuum by rotary evaporation; the solution was dried under vacuum at 40° C. by a Heidolph rotavapor. The speed of rotavapor was modulated in order to reduce bubble formation and squirt that could cause loss of product, and a dry thin film was obtained after 1-2 hours. To remove any trace of solvents, the thin film was left under vacuum for at least 16 hours at room temperature. Lipid film hydration was performed by adding different solvents (water, phosphate buffer or phosphate buffer with Tween 80) at 40-45° C. to the lipid film to form large liposome vesicles. Homogenization of these large liposome vesicles was achieved using Ika Works ULTRA-TURRAX T 25 Digital Homogenizer (Staufen, Germany), and reduction of liposome vesicles to a nano size range has been performed by extrusion using large-scale Microfluidizer® high fluid processor M-110EH at 50-60° C. and 1200 bar. This process was repeated 5 times. Sterilization of the emulsion was performed at 121° C. for 20 minutes at 1 atm. The different steps of liposome production process are represented in FIG. 1. After sterilization, the characteristics of the different liposomal vesicles were recorded: pH (using a Mettler Toledo S20 instrument); osmolality (using Osmomat 3000); particle size and zeta potential (using dynamic light scattering (DLS), also known as photon correlation spectroscopy technique—Nicomp 380 DLS).

TABLE 1

Lutein liposome emulsions composition (using 0.001% octadecylamine).

| | Composition | % w/w |
|---|---|---|
| A1 | Phospholipon 90H | 1.000 |
| | Octadecylamine | 0.001 |
| | Lutein Crystals | 0.050 |
| | Sodium phosphate monobasic dihydrate | 0.225 |
| | Sodium phosphate dibasic dihydrate | 0.685 |
| | Distilled water to | 100 g |
| A2 | Phospholipon 90H | 1.000 |
| | Octadecylamine | 0.001 |
| | Lutein Crystals | 0.050 |
| | Sodium phosphate monobasic dehydrate | 0.225 |
| | Sodium phosphate dibasic dihydrate | 0.685 |
| | Tween 80 | 0.020 |
| | Distilled water to | 100 g |

TABLE 2

Lutein liposome emulsions composition (using 0.005% octadecylamine).

| | Composition | % w/w |
|---|---|---|
| B1 | Phospholipon 90H | 1.000 |
| | Octadecylamine | 0.005 |
| | Lutein Crystals | 0.050 |
| | Distilled water to | 100 g |
| B2 | Phospholipon 90H | 1.000 |
| | Octadecylamine | 0.005 |
| | Lutein Crystals | 0.050 |
| | Sodium phosphate monobasic dihydrate | 0.225 |
| | Sodium phosphate dibasic dihydrate | 0.685 |
| | Distilled water to | 100 g |

TABLE 3

Lutein liposome emulsions composition (using 0.007% octadecylamine).

| | Composition | % w/w |
|---|---|---|
| C1 | Phospholipon 90H | 2.000 |
| | Octadecylamine | 0.007 |
| | Crystalline lutein | 0.200 |
| | Distilled water to | 100 g |

Thermostability studies. Several parameters determine the thermostability of a formulation: appearance, color, odor, osmolality and pH. All these parameters were evaluated for the emulsion prepared in two studies: a 6-month stability study performed at room temperature (21° C.±2) with 3 different time-points: 1 month, 3 months and 6 months; and a 6-month accelerated study at 52° C. with 2 different time points: 3 months and 6 months. This accelerated study was implemented under exaggerated storage conditions to simulate storage for a period much longer than 6 months.

Photostability studies. The purpose of this study was to determine if Lipo+ emulsion was sensitive to day light, by evaluating the same parameters used in the thermostability test (appearance, color, odor, osmolality and pH) according to the ICH Q1B Guideline [ICH HARMONISED TRIPARTITE GUIDELINE. 1996. STABILITY TESTING: PHOTOSTABILITY TESTING OF NEW DRUG SUBSTANCES AND PRODUCTS]. In this study, daylight degradation was simulated by irradiating samples with UV and visible light for 48 h, using a non-irradiated sample as control. Lipo+ formulation was exposed, both in amber and transparent glass vials and in triplicates, to UV/Vis light for 48 h in a photostability chamber (Industrial Laborum, Ibérica) (overall illumination ≥1.2 klux/h). According to the guideline, samples must be exposed side-by-side with a validated chemical actinometric system to ensure the minimum light exposure is attained, or for the appropriate duration of time when conditions have been monitored using calibrated radiometers/lux meters. Two 2% (w/v) solutions of Quinine-HCl (Acros Organics lot A0311764) were used as actinometric controls and were exposed to light or non-light conditions, with the latter being wrapped in aluminum foil. With this test, it is possible to determine if the exposure time was sufficient to cause any possible degradation by measurement of $Abs_{400nm}$. Statistical analysis was performed using Excel from Microsoft and standard deviation was calculated for each condition.

Cytotoxicity studies. Using an in vitro model, we evaluated the safety profile of Lipo+ emulsion. These in vitro cytotoxicity experiments were performed using a human retinal pigment epithelium cell line (ARPE-19, CRL-2302, ATCC, Manassas, Va.), as this is an established cell line corresponding to the same type of target cells that the final product will be in contact with. Cellular toxicity was assessed with WST-1 colorimetric assay (Cell Proliferation Reagent WST-1, Roche Applied Science, Mannheim, Germany) according to the manufacturer's recommendations. ARPE-19 cells were seeded at $12 \times 10^3$ cells/cm$^2$ in 96-well plates. After 12 h of growth, 4 dilutions of Lipo+ (1/15; 1/30; 1/60; 1/120) were applied for 30 and 120 min. After that, cells were washed with basal medium and incubated for 24, 48 and 72 h. After this recovery period, cell cultures were washed 4 times with basal medium, and fresh complete medium containing 10% reagent (WST-1) was added. After 3-4 h incubation, absorbance at 450 nm was measured using a TECAN plate reader. Cell culture containing 0.02% SDS was used as a positive control for cytotoxicity and complete culture medium with 100 mM PBS was used as negative control. For test samples, experiments were performed in triplicate, and for controls 6 replicates were tested. Statistical analysis was performed using Excel from Microsoft and standard deviation was calculated for each test condition.

Results

Figure 2:
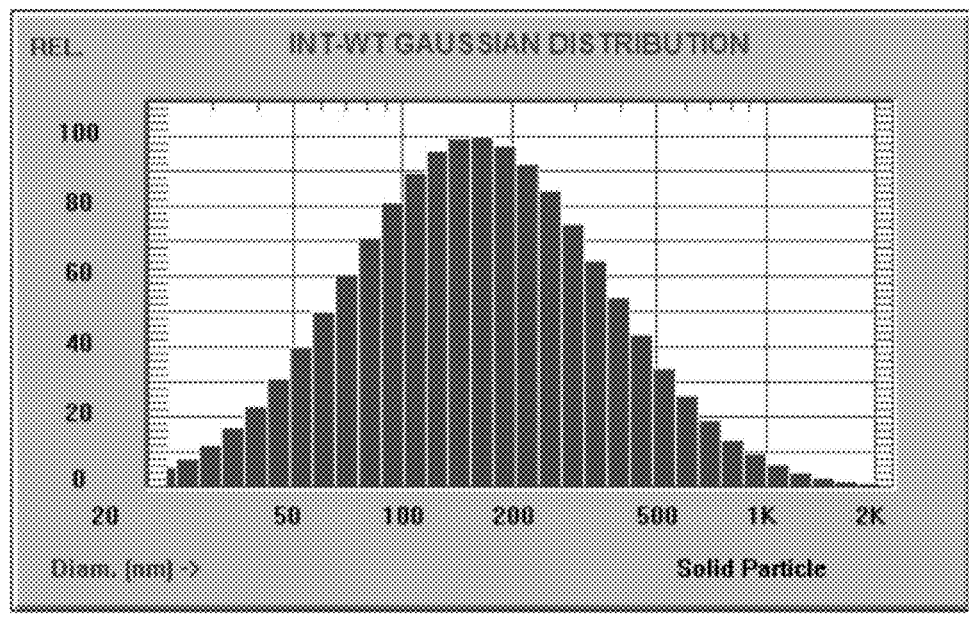
FIG. 2 is a chart of the size distribution of formulation A1 after sterilization; mean diameter of the liposomes in formulation A1 was 222.2 nm, standard deviation 180.9 nm (81.40%).
Figure 3:
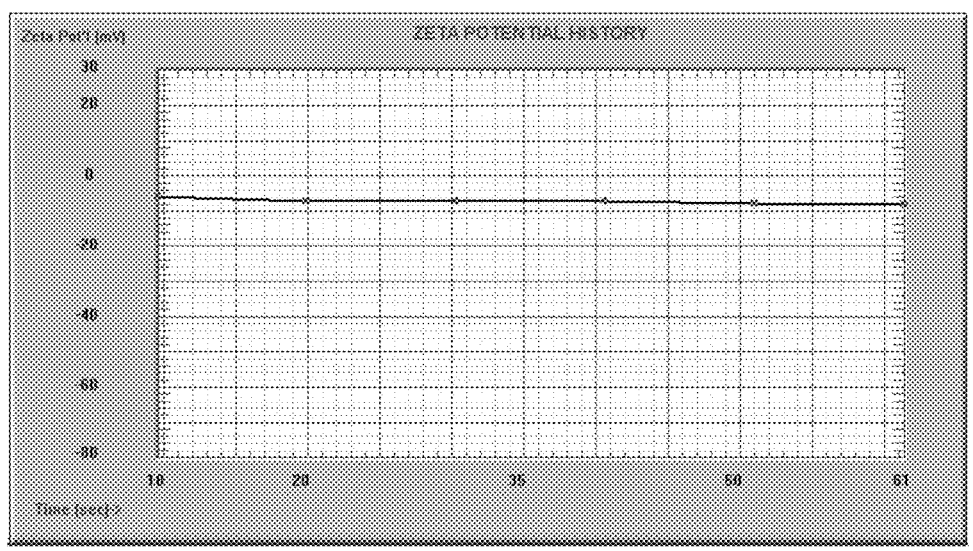
FIG. 3 is a chart of the zeta potential history of formulation A1 after sterilization; the average zeta potential of formulation A1 was −8.10 mV, the average phase shift was 6.74 rad/s and the average mobility was −0.60 M.U.

Formulation A1. After sterilization, the profile of formulation A1 was investigated. The particle size was analyzed and the mean diameter of the liposomes in this formulation was 222.2 nm (FIG. 2). The average zeta potential, which is the charge that develops at the interface between a solid surface and its liquid medium, was −8.10 mV, meaning that formulation A1 is an anionic emulsion (FIG. 3). Table 4 summarizes the characteristics of this formulation.

TABLE 4

Summary of formulation A1 characteristics after sterilization.

| pH | Osmolality (mOsM/kg) | Mean diameter (nm) | Zeta potential (mV) |
|---|---|---|---|
| 7.21 | 133 | 222 | −8.10 |

Figure 4:
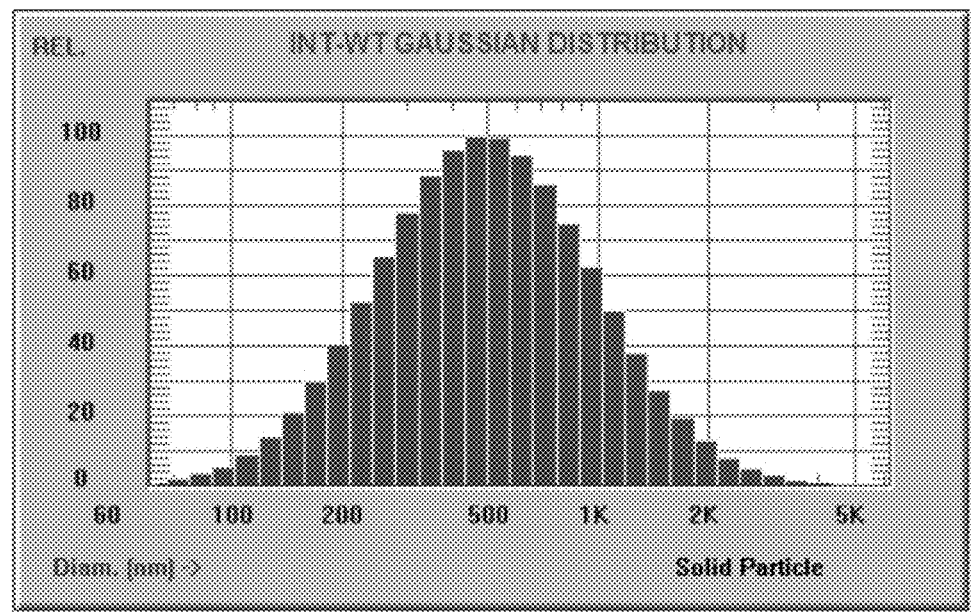
FIG. 4 is a chart of the size distribution of formulation A2 after sterilization; mean diameter of the liposomes in formulation A2 was 622.1 nm, standard deviation 424.3 nm (68.20%).
Figure 5:
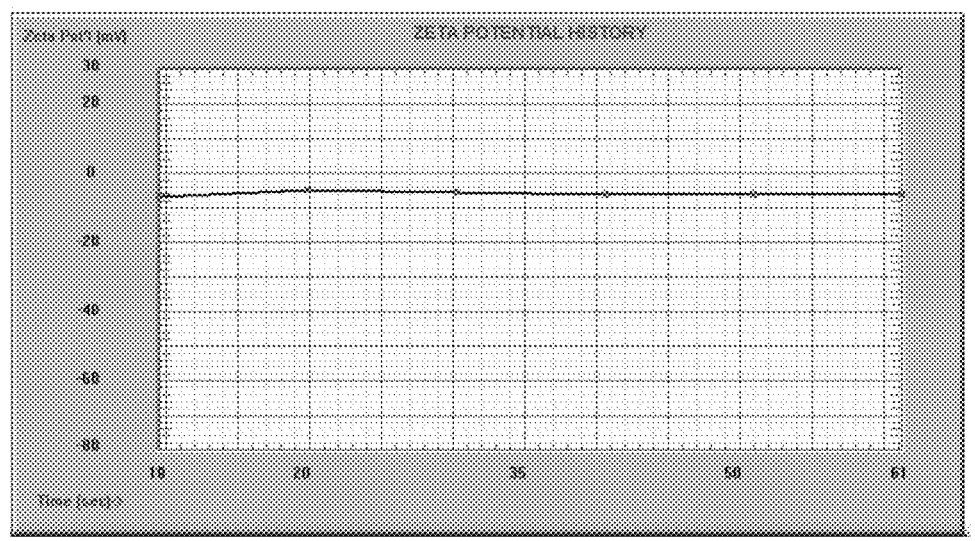
FIG. 5 is a chart of the zeta potential history of formulation A2 after sterilization; the average zeta potential of formulation A2 was −6.34 mV, the average phase shift was 5.21 rad/s and the average mobility was −0.47 M.U.

Formulation A2. Table 5 summarizes the characteristics of formulation A2 after sterilization. The particle size was analyzed and the mean diameter of the liposomes in this formulation was 622.1 nm (FIG. 4). Zeta potential analysis revealed that formulation A2 is an anionic emulsion (−6.34 mV) (FIG. 5).

TABLE 5

Summary of formulation A2 characteristics after sterilization.

| pH | Osmolality (mOsM/kg) | Mean diameter (nm) | Zeta potential (mV) |
|---|---|---|---|
| 7.20 | 136 | 622 | −6.34 |

Figure 6:
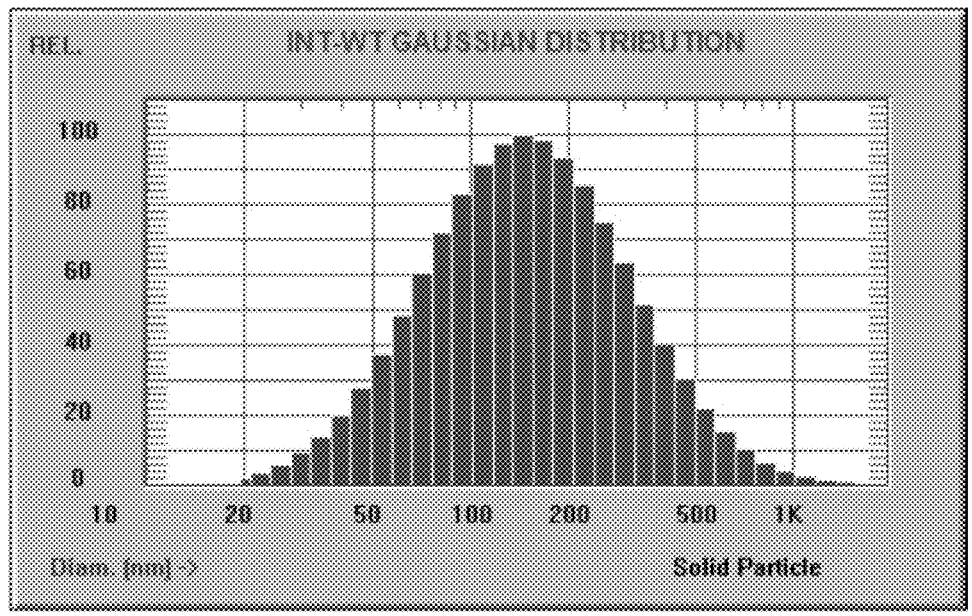
FIG. 6 is a chart of the size distribution of formulation B1 after sterilization; mean diameter of the liposomes in formulation B1 was 194.4 nm, standard deviation 142.5 nm (73.30%).
Figure 7:
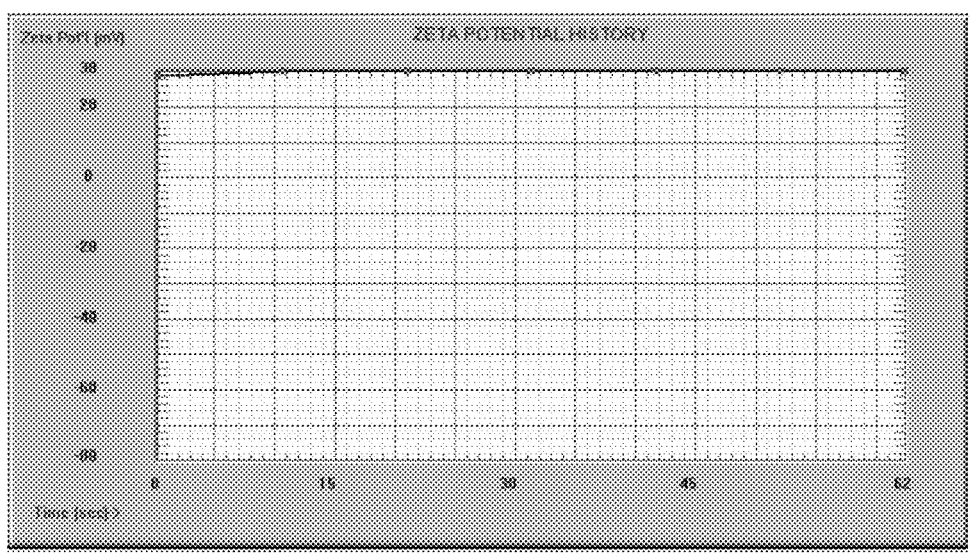
FIG. 7 is a chart of the zeta potential history of formulation B1 after sterilization; the average zeta potential of formulation B1 was +36.93 mV, the average phase shift was −37.87 rad/s and the average mobility was 2.75 M.U.

Formulation B1. The features of formulation B1 were also analyzed after sterilization. The mean diameter of liposomes in this formulation was 194.4 nm (FIG. 6). FIG. 7 shows the zeta potential analysis revealing that formulation B1 is a cationic emulsion (+36.93 mV). Table 6 reviews the profile of formulation B1.

TABLE 6

Summary of formulation B1 characteristics after sterilization.

| pH | Osmolality (mOsM/kg) | Mean diameter (nm) | Zeta potential (mV) |
|---|---|---|---|
| 6.84 | 15 | 194 | +36.93 |

Figure 8:
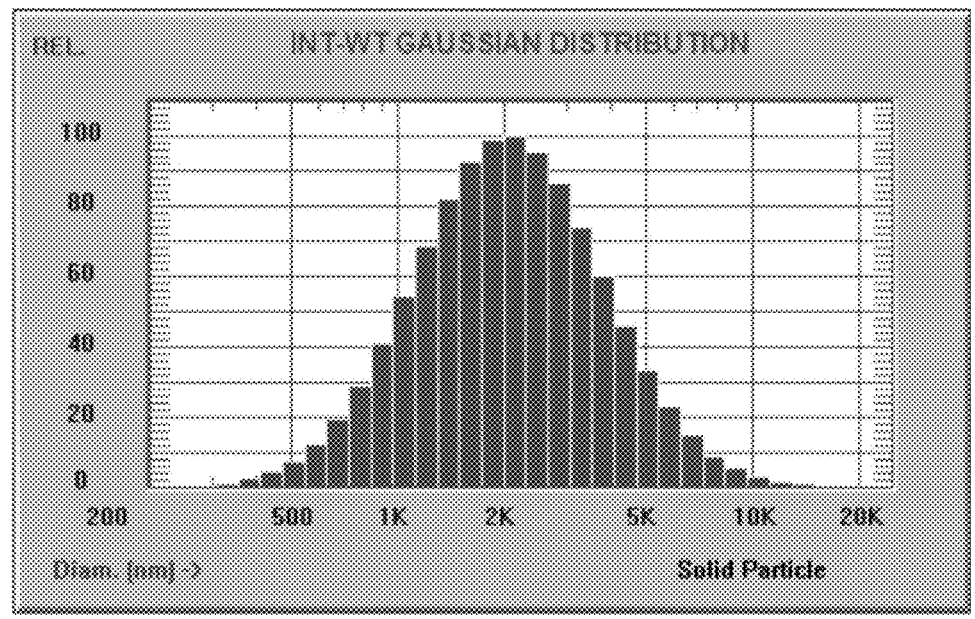
FIG. 8 is a chart of the size distribution of formulation B2 after sterilization; mean diameter of the liposomes in formulation B2 was 2481.7 nm, standard deviation 1516.3 nm (61.10%).
Figure 9:
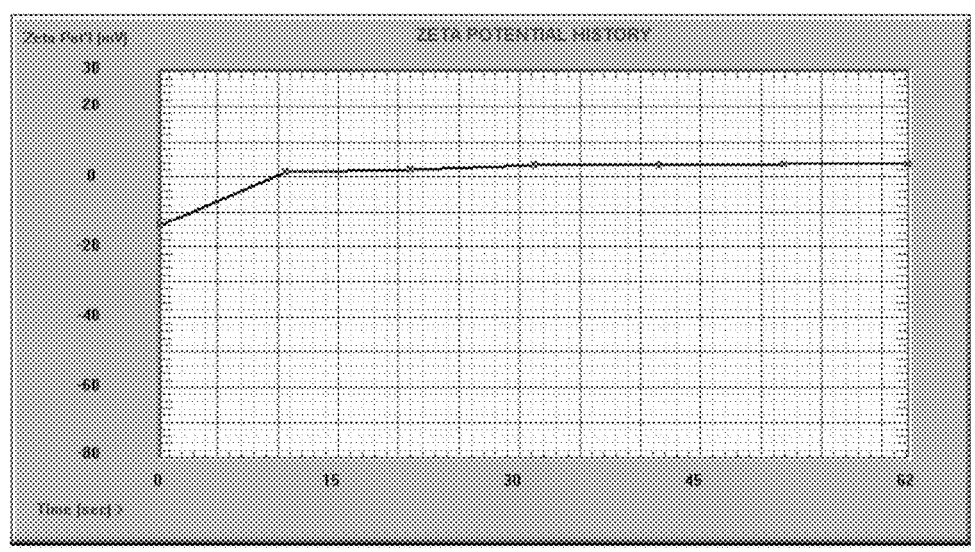
FIG. 9 is a chart of the zeta potential history of formulation B2 after sterilization; the average zeta potential of formulation B2 was +3.64 mV, the average phase shift was −3.16 rad/s and the average mobility was 0.27 M.U.

Formulation B2. Table 7 summarizes the characteristics of formulation B2 after sterilization. FIG. 8 represents the mean diameter of the liposomes; this formulation was the one with larger particle size, with an average of 2481.7 nm. Zeta potential analysis revealed that formulation B2, similarly to formulation B1, is also a cationic emulsion (+3.64 mV) (FIG. 9).

TABLE 7

Summary of formulation B2 characteristics after sterilization.

| pH | Osmolality (mOsM/kg) | Mean diameter (nm) | Zeta potential (mV) |
|---|---|---|---|
| 7.35 | 140 | 2482 | +3.64 |

Formulation C1. After sterilization, the profile of Lipo+ was characterized. Particle size was analyzed and the mean diameter of the liposomes in the formulation was 337 nm. The average zeta potential, which is the charge that develops at the interface between a solid surface and its liquid medium, was +3.45 mV, meaning it is a cationic emulsion. Table 8 summarizes the characteristics of the formulation

TABLE 8

Summary of formulation C1 characteristics after sterilization.

| pH | Osmolality (mOsM/kg) | Mean diameter (nm) | Zeta potential (mV) |
|---|---|---|---|
| 4.3 | 15 | 337 | +3.45 |

Table 9 reviews the characteristics after sterilization of all 4 formulations.

TABLE 9

Summary of the characteristics of all liposomal formulations after sterilization.

| Formulation | pH | Osmolality (mOsM/kg) | Mean diameter (nm) | Zeta potential (mV) |
|---|---|---|---|---|
| A1 | 7.21 | 133 | 222 | −8.10 |
| A2 | 7.20 | 136 | 622 | −6.34 |
| B1 | 6.84 | 15 | 194 | +36.93 |
| B2 | 7.35 | 140 | 2482 | +3.64 |
| C1 | 4.30 | 15 | 337 | +3.45 |

Thermostability studies. The stability studies evaluated if the emulsion characteristics changed over time when subjected to different temperature conditions. Lipo+ characteristics such as appearance, color, odor, pH and osmolality were evaluated over 6 months in two independent studies conducted at room temperature (≈20° C.) and 52° C. (accelerated study).

Figures 10A, 10B:
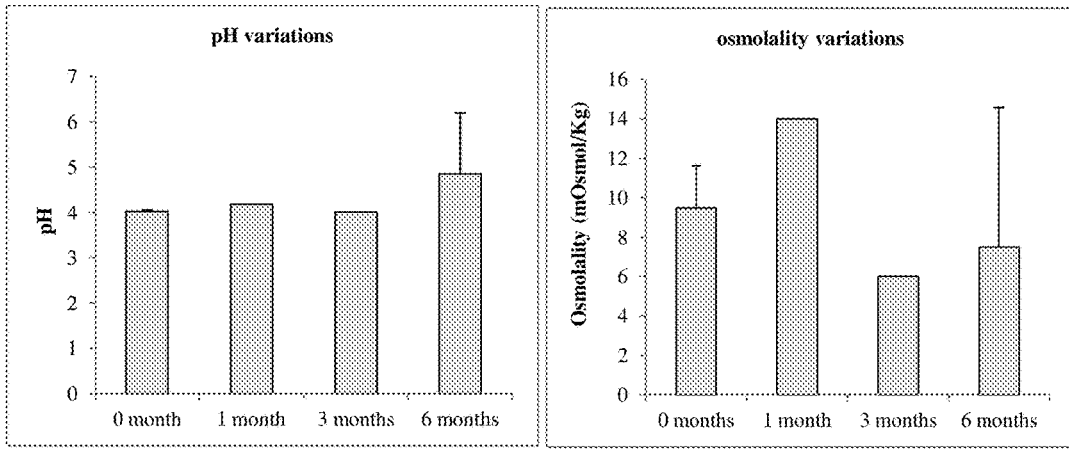
FIGS. 10A and 10B are charts of the pH and osmolality variations, respectively, of Lipo+ samples for 6 months at room temperature; the standard errors from two replicates are shown as error bars.

Lipo+ characteristics after 1, 3 and 6 months at room temperature are summarized in Table 10 and FIG. 10. For the first 3 months, the initial pH was maintained and minor changes were detected after 6 months. For the osmolality, changes were more pronounced, suggesting that improvements of the formulation might be required to stabilize osmolality.

TABLE 10

Lipo+ characteristics at the beginning of the study (time zero) and after 1, 3 and 6 months at room temperature.

| | time = 0 | | time = 1 month | | time = 3 months | | time = 6 months | |
|---|---|---|---|---|---|---|---|---|
| Test | 1 | 2 | 1 | 2 | 1 | 2 | 1 | 2 |
| Appearance | viscous solution | viscous solution | viscous solution | viscous solution | viscous solution | viscous solution | viscous solution | viscous solution |
| Color | orange | orange | orange | orange | orange | orange | orange | orange |
| Odor | herbal | herbal | herbal | herbal | herbal | herbal | herbal | herbal |

Figures 11A, 11B:
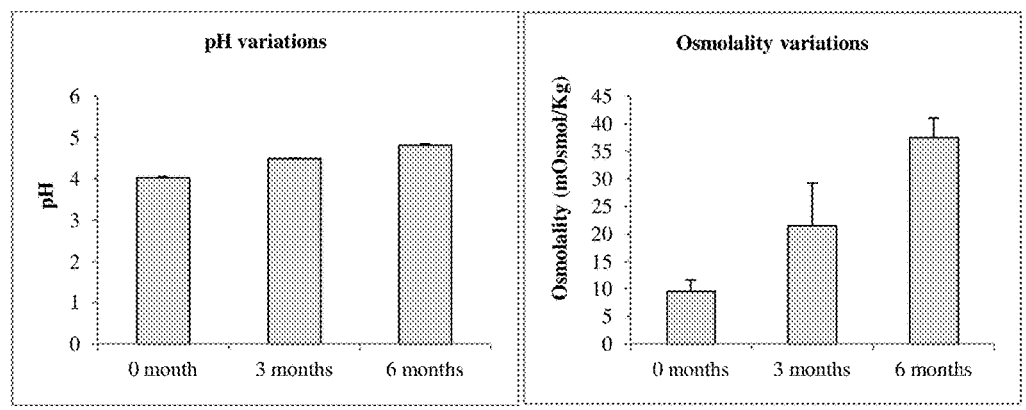
FIGS. 11A and 11B are charts of the pH and osmolality variations, respectively, of Lipo+ samples for 6 months at room temperature; the standard errors from two replicates are shown as error bars.

For the 52° C. stability study, results are presented in Table 11 and FIG. 11, for the 3 and 6-month time points. In this study, the formulation showed to be unstable at higher temperatures as color and appearance changed after 3 months at 52° C. Again, pH showed less variance through time than osmolality, indicating this parameter must be improved.

TABLE 11

Lipo+ characteristics at the beginning of the study (time zero) and after 3 and 6 months at 52° C.

|  | time = 0 | | time = 3 months | | time = 6 months | |
| --- | --- | --- | --- | --- | --- | --- |
| Test | 1 | 2 | 1 | 2 | 1 | 2 |
| Appearance | viscous solution | viscous solution | Solution with sediments | Solution with sediments | Solution with sediments | Solution with sediments |
| Color | orange | orange | white | white | Light orange | Light orange |
| Odor | herbal | herbal | herbal | herbal | herbal | herbal |

Photostability studies. Lipo+ and control samples were subjected to light (UV/Vis) in a photostability chamber. After 48 hours of exposure, degradation of Quinine-HCl was evaluated through measurement of $Abs_{400nm}$. This parameter was above 0.5 ($Abs_{400nm}$=0.596) indicating the exposure time was sufficient to cause degradation in samples exposed to the same conditions as the actinometric control.

Figures 12A, 12B:
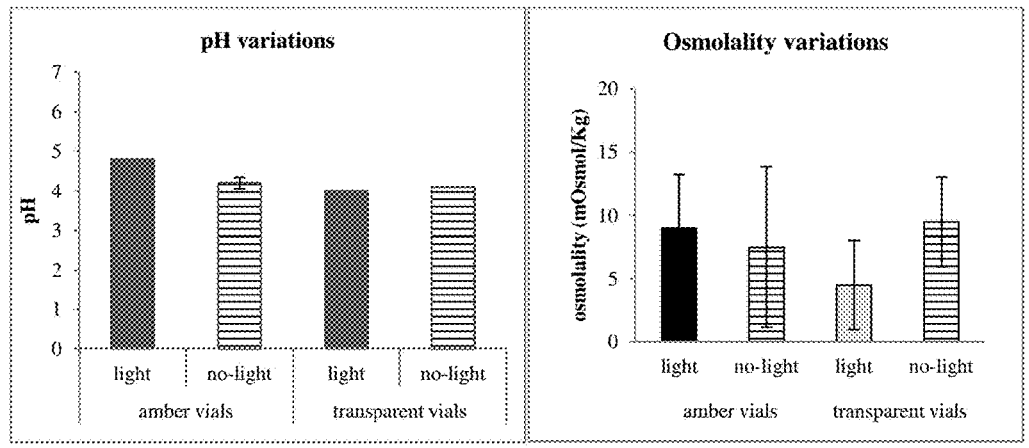
FIGS. 12A and 12B are charts of the pH and osmolality variations, respectively, after the photostability experiment; Lipo+ pH and osmolality have not changed after the light exposure when the emulsion was maintained in amber nor transparent vials; the standard errors from two replicates are shown as error bars.

The appearance, color and odor of Lipo+ was assessed and revealed the formulation was stable after the exposure maintaining the initial characteristics (appearance: viscous homogeneous solution; color: orange, odor: herbal) when maintained in amber or transparent vials (Table 12). Likewise, the pH values did not change significantly for transparent vials exposed or not to light. For amber vials, a change in pH was seen between exposed vials and non-exposed vials. Regarding the osmolality values, changes were more visible between light and no-light exposure vials, for amber or transparent. The results are shown in FIG. 12.

TABLE 12

Lipo+ characteristics after photostability studies: comparison between light and non-light exposed samples in amber or transparent glass vials.

|  | Light-exposed | | Non-light exposed | |
| --- | --- | --- | --- | --- |
| Test | Amber vials | Transparent vials | Amber vials | Transparent vials |
| Appearance | viscous solution | viscous solution | viscous solution | viscous solution |
| Color | orange | orange | orange | orange |
| Odor | herbal | herbal | herbal | herbal |

Cytotoxicity studies. In vitro cytotoxicity testing was performed on Lipo+ using the direct contact method in human retinal pigment epithelial cell culture lines (ARPE-19). Cytotoxicity was measured using WST-1 method. This assay identifies cellular metabolic response changes according to mitochondrial activity, thereby giving a very approximate assessment of in vitro cytotoxicity of this type of solutions. Cells were washed and allowed to recover for 24, 48, and 72 hours after the contact with Lipo+ dilutions for 30 and 120 min, as well as with positive and negative controls. The dilutions used were chosen having in consideration the volume of liquid inside the eye (4 mL) and inferring the amount of the solution that will penetrate in the patient's eye after the iontophoretic application [Molokhia S. A., Jeong E. K., Higuchi W. I., Li S. K. 2009. Transscleral iontophoretic and intravitreal delivery of a macromolecule: study of ocular distribution in vivo and postmortem with MRI. Exp Eye Res. 88:418-425].

Figure 13:
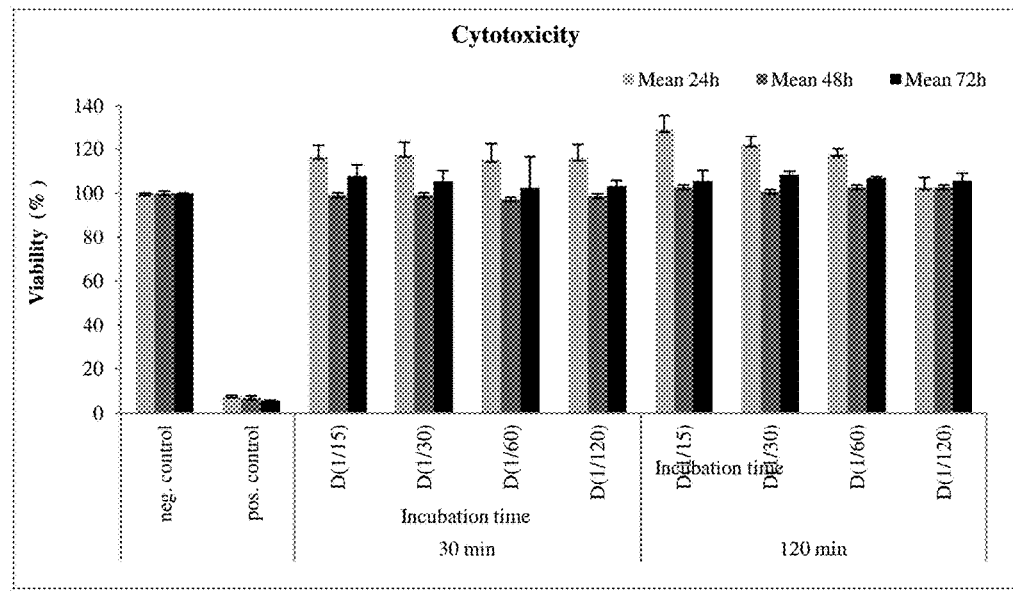
FIG. 13 is a chart of cell viability after 30 and 120 min of incubation with Lipo+ dilutions; medium with 0.02% SDS and 100 mM PBS was used as a positive and negative control respectively; the standard errors from triplicate experiments are shown as error bars.

As depicted in FIG. 13, the results reveal no cytotoxic effect of Lipo+ since cell viability was not reduced with any of the dilutions tested in direct contact with the cells, in comparison with the controls. The samples tested were dilutions of the final sterilized emulsion that is intended to be used for the subsequent experiments in the iontophoresis project.

Discussion

Our goal is to develop a new way of delivering a high concentration of lutein/zeaxanthin to the retina so that its presence in the macula can be enhanced significantly, with the aim of preventing the onset and/or progression of AMD and also to protect the retinal endothelial cells. For that, we will use ocular iontophoresis, which is a technique based on the general principle that similar charges repel each other and different charges attract each other.

The Lipo+ emulsion was produced considering that has been demonstrated that positive particles are better candidates for iontophoretic application as drug carrier than negatively charged particles due to higher penetration into ocular tissues [Eljarrat-Binstock E., Orucov F., Aldouby Y., Frucht-Pery J., Domb A. J. 2008. Charged nanoparticles delivery to the eye using hydrogel iontophoresis. J Control Release. 126:156-161]. Furthermore, the electrical field forces the positive charged molecules to move into eye membranes that are negatively charged [Nicoli S., Ferrari G., Quarta M., Macaluso C., Santi P. 2009. In vitro transscleral iontophoresis of high molecular weight neutral compounds. Eur J Pharm Sci. 36:486-492]. In order to overcome the difficulty of lutein delivery trough iontophoresis (since this molecule has no charge) we have produced positively charged liposome (zeta potential=+3.45 mV) vesicles that behave as carriers of lutein molecules. Previous studies have shown that at pH 3, transport in the cathode-to-anode direction was significantly higher than that from anode-to-cathode [Gungor S., Delgado-Charro M. B., Ruiz-Perez B., Schubert W., Isom P., Moslemy P., Patane M. A., Guy R. H. 2010. Trans-scleral iontophoretic delivery of low molecular weight therapeutics. J Control Release. 147:225-231], suggesting that Lipo+ (pH=4.3) has the indicated characteristics to be used in the iontophoretic delivery of lutein.

In order to better understand the characteristics of the new formulation, as well as infer the shelf-life of the product, two stability studies for 6 months were performed. Moreover, a photostability study of the final formulation was also performed. From all studied characteristics, only osmolality showed to be highly affected by temperature and/or light. These results indicate the need of stabilizing the osmolality of this formulation.

Since this new formulation will be used as active ingredient in ocular iontophoretic applications, it is very important to assess the safety profile of Lipo+ when in contact with the target cells of the human eye. In vitro cytotoxicity experiments were performed in vitro, using a human retinal pigmented epithelial cell line incubated with different Lipo+ dilutions. The results showed no cytotoxic effect on the cell line studied for different incubation times and dilutions, demonstrating that Lipo+ have a safe profile in cell culture models. This results suggest this Lipo+ formulation is a promising candidate to be a used for intraocular delivery of lutein/zeaxanthin.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

I claim:

1. A method of producing positively charged liposome vesicles for use as carriers of at least one carotenoid, comprising the steps of:
   (a) dissolving in a solvent a mixture of hydrogenated phospholipids, a cationic excipient and the at least one carotenoid to form a composition;
   (b) drying the composition to remove the solvent;
   (c) hydrating the dried composition to form liposome vesicles and optionally homogenizing the liposome vesicles; and
   (d) sterilizing the vesicles.

2. The method of claim 1, wherein the cationic excipient is octadecylamine.

3. The method of claim 1, wherein the carotenoid is selected from the group consisting of lutein and zeaxanthin.

4. A method delivering a lipophilic molecule to ocular tissues, comprising the step of delivery of the vesicles of claim 1 using iontophoresis.

5. The method of claim 4, wherein the lipophilic molecule is crystalline lutein and wherein the vesicles are transported through cornea and sclera cells.

6. The method according to claim 1 wherein following sterilization, the liposome vesicles remain stable for at least six months at room temperature.

* * * * *